United States Patent
Ek et al.

(10) Patent No.: US 12,369,845 B2
(45) Date of Patent: Jul. 29, 2025

(54) METHOD AND SYSTEM FOR ASSESSMENT OF A BLOOD FLOW

(71) Applicant: PUsensor AB, Linköping (SE)

(72) Inventors: Anna-Christina Ek, Linköping (SE); Margareta Lindgren, Ljungsbro (SE); Johannes Walfridsson, Linköping (SE); Tova Persson, Linköping (SE)

(73) Assignee: PUsensor AB, Linköping (SE)

( * ) Notice: Subject to any disclaimer, the term of this patent is extended or adjusted under 35 U.S.C. 154(b) by 815 days.

(21) Appl. No.: 17/042,744

(22) PCT Filed: Mar. 20, 2019

(86) PCT No.: PCT/SE2019/050251
§ 371 (c)(1),
(2) Date: Sep. 28, 2020

(87) PCT Pub. No.: WO2019/190378
PCT Pub. Date: Oct. 3, 2019

(65) Prior Publication Data
US 2021/0068743 A1   Mar. 11, 2021

(30) Foreign Application Priority Data
Mar. 28, 2018 (SE) .................... 1850354-0

(51) Int. Cl.
*A61B 5/00* (2006.01)
*A61B 5/026* (2006.01)
*A61B 5/0295* (2006.01)

(52) U.S. Cl.
CPC ............ *A61B 5/447* (2013.01); *A61B 5/0053* (2013.01); *A61B 5/0261* (2013.01);
(Continued)

(58) Field of Classification Search
CPC ...... A61B 2562/0247; A61B 2562/046; A61B 2562/0053; A61B 2562/0261;
(Continued)

(56) References Cited

U.S. PATENT DOCUMENTS 8,133,177 B2   3/2012 LaPlante et al.
2004/0054303 A1   3/2004 Taylor
(Continued)

FOREIGN PATENT DOCUMENTS

CN   1398175 A   2/2003
CN   103327894 A   9/2013
(Continued)

OTHER PUBLICATIONS

Extended European Search Report received for EP Application No. 19775199.3, dated Nov. 22, 2021.
(Continued)

*Primary Examiner* — Michael T Rozanski
(74) *Attorney, Agent, or Firm* — MARSHALL, GERSTEIN & BORUN LLP

(57) ABSTRACT

A method and system for assessment of a blood flow in an area of the skin and underlying tissue of a patient. The method including subjecting the assessed area to at least two different pressure states. The method further includes obtaining blood flow data related to the assessed area while subjecting the assessed area to the at least two different pressure states, wherein the blood flow data is obtained by means of photoplethysmography, and assessing the risk of pressure ulcers on the patient based on assessment of the blood flow data obtained for the at least two different pressure states.

20 Claims, 4 Drawing Sheets

(52) U.S. Cl.
CPC .......... *A61B 5/0295* (2013.01); *A61B 5/6833* (2013.01); *A61B 5/7275* (2013.01); *A61B 2562/0247* (2013.01)

(58) Field of Classification Search
CPC ...... A61B 2562/0295; A61B 2562/447; A61B 2562/6833; A61B 2562/6892; A61B 2562/7275
See application file for complete search history.

(56) References Cited

U.S. PATENT DOCUMENTS

| | | |
|---|---|---|
| 2004/0249290 A1 | 12/2004 | Shani et al. |
| 2006/0058690 A1 | 3/2006 | Bartnik et al. |
| 2006/0287603 A1 | 12/2006 | Bartnik et al. |
| 2012/0220878 A1 | 8/2012 | Sullivan et al. |
| 2016/0228050 A1 | 8/2016 | Sugla et al. |
| 2017/0027498 A1 | 2/2017 | Larson et al. |
| 2017/0224261 A1 | 8/2017 | Sarrafzadeh et al. |
| 2018/0014774 A1 | 1/2018 | Hollopeter et al. |
| 2018/0369041 A1* | 12/2018 | Sheth .................. A61G 7/05776 |

FOREIGN PATENT DOCUMENTS

| | | |
|---|---|---|
| CN | 107280682 A | 10/2017 |
| KR | 20060007507 A | 1/2006 |
| KR | 20110070139 A | 6/2011 |

OTHER PUBLICATIONS

International Search Report and Written Opinion received for PCT/SE2019/050251 dated Jun. 4, 2019.
Japanese Office Action, Japanese Application No. 2020-545355, dated Feb. 13, 2023.
Akbari et al., "Designing and Constructing Blood Flow Monitoring System to Predict Pressure Ulcers on Heel," Journal of Biomedical Physics Engineering, vol. 4, No. 2, Jun. 8, 2014, pp. 61-68.
Chinese Office Action, Chinese Application No. 2019800170696, dated Nov. 16, 2023.

* cited by examiner

Fig 5a
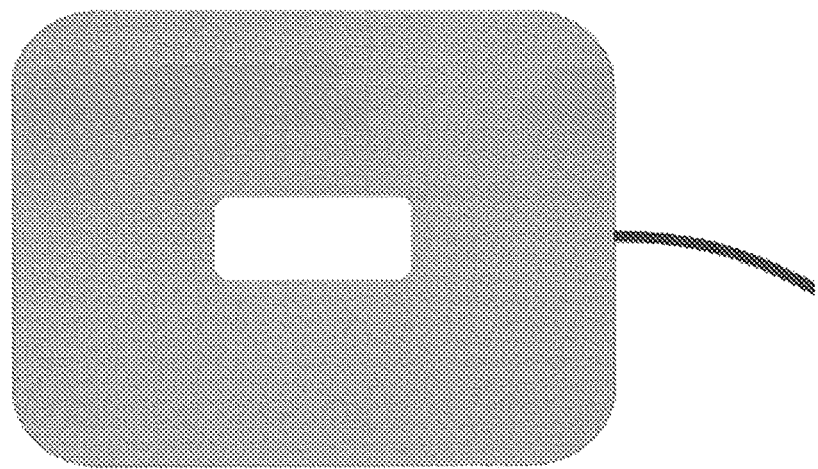
Fig 5b
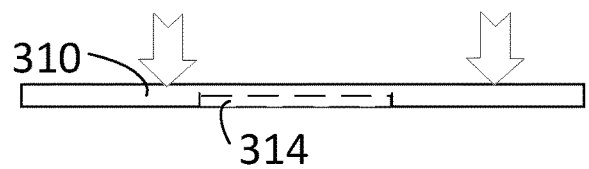
Fig 5c
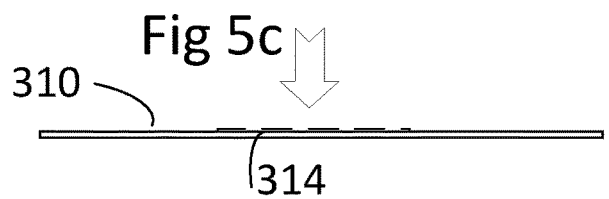
Fig 6
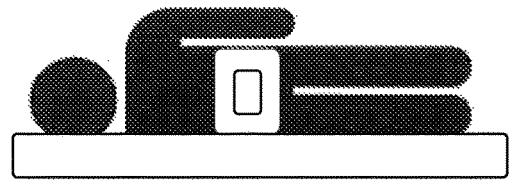
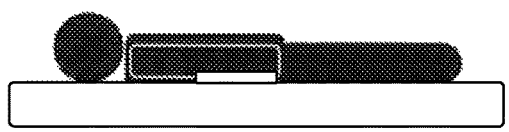
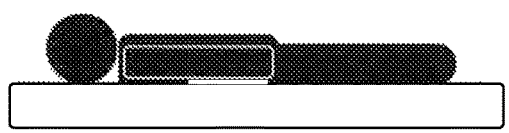

METHOD AND SYSTEM FOR ASSESSMENT OF A BLOOD FLOW

The present application is a national stage entry of International Patent Application No. PCT/SE2019/050251, filed Mar. 20, 2019, which claims priority to and the benefit of the filing date of Swedish Patent Application No. 1850354-0, filed Mar. 28, 2018. The entire disclosure of each of these applications is hereby expressly incorporated by reference herein for all uses and purposes.

TECHNICAL FIELD

The present disclosure relates to a method and system for assessment of a risk of developing pressure ulcers.

BACKGROUND ART

Pressure ulcers are injuries to skin and underlying tissue resulting from prolonged pressure on the skin. Those are most often developed on skin that covers bony areas of the body, such as the heels, ankles, hips and sacrum.

People most at risk of developing pressure ulcers are those with a medical condition that limits their ability to change positions or those who spend most of their time in a bed or chair. Immobile individuals frequently develop painful pressure ulcers. Moreover, pressure ulcers cause high costs for the health care system.

SUMMARY OF THE INVENTION

The present disclosure relates to an improved method for assessment of a risk of developing pressure ulcers.

This has been achieved by means of a method for assessment of a blood flow in an area of the skin and underlying tissue of a patient. The method comprises a step of subjecting the assessed area to at least two different pressure states, wherein the different pressure states are obtained by the patient's weight pressuring against a support on which the patient is placed and an expandable element at least partly circumventing the assessed area and expandable a direction from the support against the patient to substantially eliminate a pressure on the patient's body from the support in the area at least partly circumventing the assessed area. The method further comprises the steps of obtaining (S8) blood flow data related to the assessed area while subjecting the assessed area to the at least two different pressure states, wherein the blood flow data is obtained by means of photoplethysmography and assessing (S9) the risk of pressure ulcers on the patient based on assessment of the blood flow data obtained for the at least two different pressure states.

The method is easy to use and give rise to a decreased discomfort for the patient. The patient may lie down in the same position during the entire measurement.

In different embodiments, in the first pressure state substantially no pressure is provided in the assessed area. Thereby, a measurement of the basal blood flow is obtained and any blood flow measured under pressure can be related to the basal blood flow.

In different embodiments, in the second pressure state, the body weight pressures against the assessed area. Accordingly, a measurement is provided at least more or less reflecting the daily situation when the patient spends most of his/her time in a bed or chair.

Comparing the basal blood flow to the blood flow reflecting the daily situation for the patient provides for a risk assessment with an increased reliability.

The first and the second pressure states may be obtained in the above order to decrease the risk that the measurement of the basal blood flow is disturbed by a previous load to the assessed area.

In different embodiments, the method comprises a step of controlling the expandable element at least between a first expansion state corresponding to the first pressure state and a second expansion state corresponding to the second pressure state.

By this automatization, the requirements on education etc of personnel using the method may be decreased.

In different embodiments, the method comprises a step of obtaining pressure data a step of identifying (S7) the respective pressure states based on the obtained pressure data. The step of assessing the risk of pressure ulcers is then made based on blood flow data obtained for the identified at least two different pressure states.

In practice, the blood flow data may be obtained by: illuminating the skin and underlying tissue with the light from a LED, and measuring the amount of light reflected to a photodiode.

The method may further comprise the steps of: providing the expandable element having a controllable expansion state, providing a sensor element for obtaining the blood flow data using photoplethysmography, positioning the expandable element in relation to the patient such that the patient's weight provides the pressure to the assessed area in dependence of the expansion state of the expandable element, obtaining blood flow data related to the assessed area using the sensor element, and assessing the risk of pressure ulcers on the patient based on assessment of the blood flow data obtained for at least two different expansion states of the expandable element.

When the sensor element is not integrated with expandable element, the method further comprises a step of attaching the sensor element to the skin of the assessed area.

The present disclosure further relates to a software for performing a method as defined in any of the preceding claims.

The present disclosure further relates to a system for assessment of a blood flow in an area of the skin and underlying tissue of a patient. The system comprises a sensor plate having at least one blood flow sensor obtained by means of photoplethysmography; and an expandable element (310) having a controllable expansion state. The expandable element is arranged to form a frame at least partly circumventing the sensor plate. The configuration of the expandable element secures that the assessed area is subjected to at least two different pressure states obtained by the patient's weight pressuring against a support on which the patient is placed and an expansion of the expandable element in a direction from the support against the patient to substantially eliminate a pressure on the patient's body from the support in the area at least partly circumventing the assessed area. The system further comprises a computing system arranged to perform data processing of said blood flow data.

The at least one blood flow sensor is arranged to obtain blood flow data while subjecting the assessed area to the at least two different pressure states. The computing system is arranged to assess the risk of pressure ulcers on the patient, based on assessment of the blood flow data for the at least two different pressure states.

The system may further comprise a Data Acquisition System, DAS, connected to the sensor plate, said Data Acquisition System being arranged for data conditioning and converting of said blood flow data, wherein the computing system is connected to the Data Acquisition System.

The sensor plate may be flexible and arranged to follow the curvature of the skin.

The sensor plate may be provided with an adhesive for attachment to the patient.

The sensor plate may further comprises a plurality of LED-diodes of at least two different wavelengths and at least one photodetector.

The at least one photodetector may be arranged to receive data from a plurality of LEDs and to measure the data from each LED individually.

The system may further comprise at least one pressure sensor obtaining pressure data. The computing system is arranged to identify the respective pressure states based on the obtained pressure data and to assess the risk of pressure ulcers on a patient based on blood flow data obtained for the identified at least two different pressure states.

The present disclosure further relates to a control element for assessment of a blood flow in an area of the skin and underlying tissue of a patient. The control element comprises an interface arranged to receive blood flow data from at least one sensor obtained by means of photoplethysmography. The blood flow data is obtained from the assessed area subjected to at least two different pressure states obtained by the patient's weight pressuring against a support on which the patient is placed and an expansion of an expandable element in a direction from the support against the patient to at least substantially eliminate a pressure on the patient's body from the support in the area at least partly circumventing the assessed area. The control element further comprises a processor arranged to perform data processing of said blood flow data to assess the risk of pressure ulcers on the patient, based on assessment of the blood flow data for the at least two different pressure states.

BRIEF DESCRIPTION OF THE DRAWINGS

FIG. 5a illustrates a view from above of an example of an expandable element for use in assessing a tissue.

FIG. 5b illustrates a side view of the expandable element of FIG. 5a in an expanded state.

FIG. 5c illustrates a side view of the expandable element of FIG. 5a in a non-expanded state.

FIG. 6 illustrates an example of an application for the method for assessment of a blood flow as disclosed in relation to FIG. 1.

DETAILED DESCRIPTION

Figure 1:
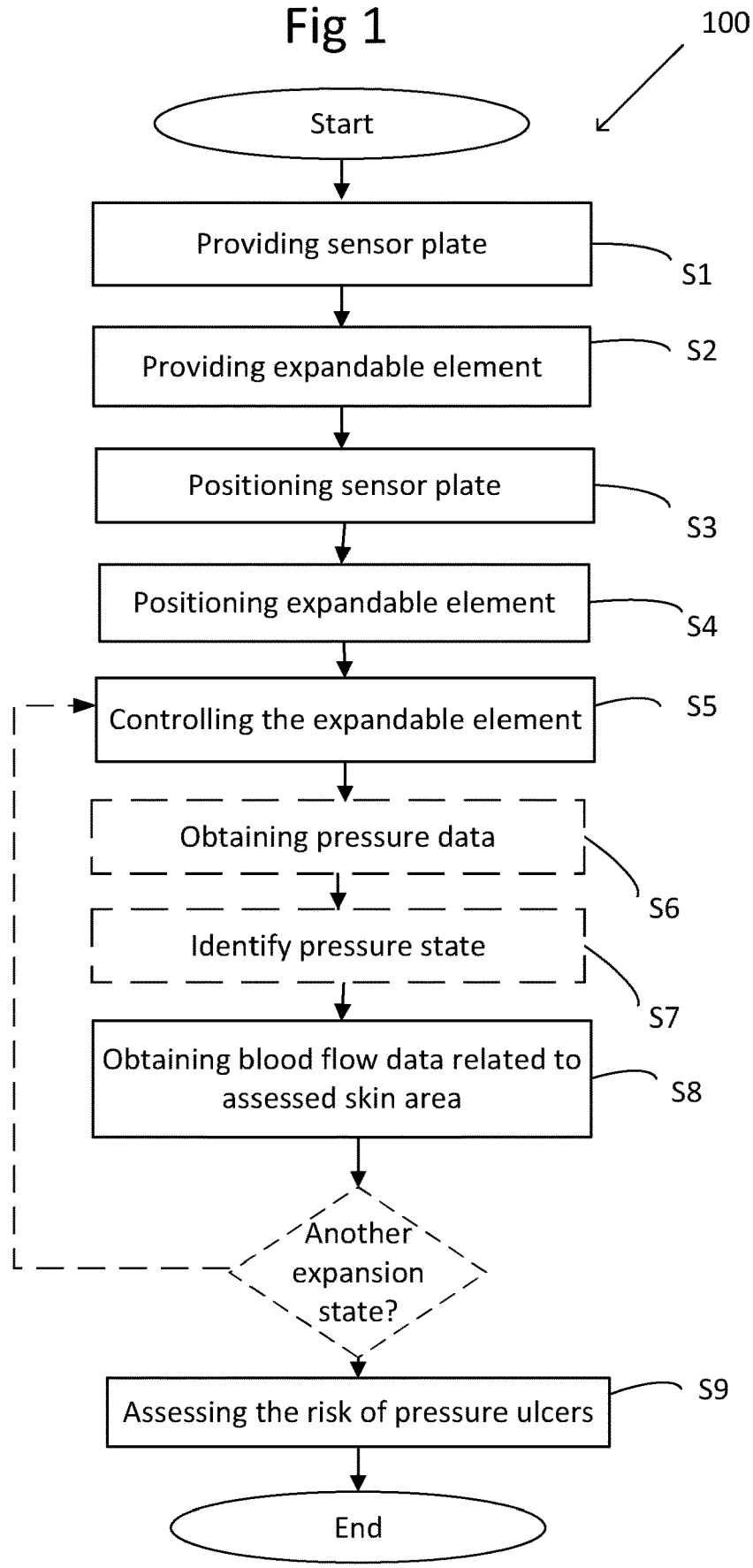
FIG. 1 is a flow chart illustrating an example of a method for assessment of a blood flow.

FIGS. 1 and 6 disclose an example of a method for assessment of a blood flow in an area of the skin and underlying tissue of a patient. The method assesses a risk of developing pressure ulcers on the patient based on the blood flow data.

Pressure ulcers are injuries to skin and underlying tissue resulting from prolonged pressure on the skin. Those are most often developed on skin that covers bony areas of the body, such as the heels, ankles, hips and sacrum.

The exemplified method for assessment of a blood flow in a skin area to assess a risk of developing pressure ulcers is easy to use and give rise to a decreased discomfort for the patient.

The method is based on the concept that the assessed skin area is subjected to at least two different pressure states, wherein the different pressure states are obtained by the patient's weight pressuring against a support on which the patient is placed and an expandable element. The expandable element is at least partly circumventing the assessed area. The expandable element is expandable in a direction from a plane of the support towards the patient to at least substantially eliminate a pressure on the patient's body from the support in the area at least partly circumventing the assessed skin area. The expansion state of the expandable element controls the body pressure applied to the assessed skin area of the patient.

The at least two different pressure states applied to the assessed skin area may comprise a first pressure state where the assessed skin area is subjected to substantially no pressure. In this first pressure state, the assessed skin area is lifted from the support on which the patient is placed by means of the expandable element. The assessed skin area is in an example lifted from the support no more than enough to substantially eliminate a pressure on the assessed skin area of the patient's body from the support. If lifting the assessed skin area more than necessary above the support, this requires providing a higher pressure than necessary to parts of the skin and underlying tissue around the assessed skin area by means of the expandable element. This may lead to a risk that the blood flow within the assessed area is affected by the pressure subjected to the skin and underlying tissue parts around the assessed area. It is generally desired that the expandable element is designed to effect the blood flow in the assessed skin area as little as possible.

The at least two different pressure states applied to the assessed area may comprise a second pressure state, wherein the body weight provides pressure to the assessed area. Characteristically, the thickness of the expandable element in this state is as thin as possible.

Blood flow data related to the assessed area is obtained while subjecting the assessed area to the at least two different pressure states. The blood flow data is obtained by means of photoplethysmography. The blood flow data may be obtained only by means of photoplethysmography.

The risk of pressure ulcers on the patient is assessed based on assessment of the blood flow data obtained for the at least two different pressure states.

Thus, in accordance with the method, blood flow data is obtained while at least two different pressures are applied to the assessed skin area, wherein the pressure is obtained by using the patient's weight. In one example, one of the pressures under which the blood flow data is obtained corresponds to the patient's weight. Another pressure under which the blood flow data is obtained may correspond to substantially no pressure from the patient's body weight.

The sensor plate is placed on the skin area to be assessed. The design of the sensor plate will be discussed more in detail in relation to FIG. 4.

In the illustrated examples, the method for assessment of a blood flow in an area of the skin and underlying tissue of a patient comprises a step of providing S1 a sensor element for obtaining blood flow data. As stated above, the sensor plate may comprise a blood flow sensor element arranged to obtain blood flow data based on photoplethysmography.

The method further comprises a step of providing S2 an expandable element having a controllable expansion state. The expandable element may form a rim for the sensor plate. Thus the, sensor element is intended to be partly or entirely surrounded by the expandable element. The expandable element may be fastened to the sensor plate, form a unit integrated with the sensor plate or be a unit physically separated from the sensor plate.

The method further comprises a step of positioning S4 the expandable element in relation to a patient such that the patient's weight provides the pressure to the assessed area in dependence of the expansion of the expandable element in FIG. 6 (upper picture) it is illustrated that the expandable element is positioned at the patient's back. The expandable element is in an example positioned at the sacrum of the patient.

Further, the sensor plate is arranged S3 at least partly circumvented by the expandable element to abut against the skin of the patient. This step may comprise of attaching the sensor plate to the skin for example by means of an adhesive. The attachment may for example be provided by means of a double sided tape. The adhesive preferably is substantially transparent to the rays emitted by and reflected to a blood flow sensor element of the sensor plate in order not to disturb the measurements.

The method comprises further a step of controlling S5 expansion of the expandable element. Characteristically, the expandable element is controlled to different expansion states. For example, in a first expansion state substantially no pressure may be applied to the assessed area. A second expansion state may be a non-expanded or deflated state, where the body weight provides pressure to the assessed area.

In FIG. 6, the lower pictures, the patient is lying on his back. In the lower left picture the expandable element is expanded. The body weight of the patient exercises pressure against the expandable element but not on the assessed area wherein the skin is provided with the sensor plate. Thus, the expanded expandable element protects the sensor element at least partly circumvented by the expansion element from the body weight of the patient. Accordingly, substantially no pressure is applied to the assessed area where the skin is provided with the sensor plate.

In the lower right picture the expandable element is not expanded and the body weight of the patient exercises pressure against the support in the assessed skin area where the skin is provided with the sensor plate.

The method comprises further a step of obtaining S8 blood flow data related to the assessed skin area in the at least two different pressure states. The obtaining of blood flow data may be provided upon determination that the expandable element is in the respective state. In accordance therewith, when it has been determined that the respective expansion state has been reached, the obtaining of blood flow data may be initiated for that expansion state. The obtaining of blood flow data may be performed during a pre-set amount of time. Alternatively, blood flow data may be continuously obtained during the entire procedure.

As stated above, the blood flow data is obtained by means of photoplethysmography (PPG). In detail, a PPG is an optically obtained volumetric measurement of an organ. A PPG may be obtained by illuminating the skin and underlying tissue, and measuring changes in light absorption.

In systole in each cardiac cycle the heart pumps blood to the tissue. Even though this pressure pulse is somewhat damped by the time it reaches the skin, it is enough to distend the arteries and arterioles in the subcutaneous tissue. The change in volume caused by the pressure pulse is detected by illuminating the skin and underlying tissue with the light from a light-emitting diode (LED) and then measuring the amount of light reflected to a photodiode. Each systole cycle appears as a peak. Thus, these pressure pulses are in the present disclosure compared while the skin is subjected to different external pressures caused by the patient's weight, as discussed above.

The method may further comprise a step of obtaining S6 pressure data related to the body pressure applied to the assessed skin area. The pressure data may be provided by measuring the body pressure applied to the assessed skin area. The pressure may for example be measured by means of at least one pressure sensor. The at least one pressure sensor may be formed at the sensor plate which also comprises the blood flow sensor element.

The respective pressure states may be identified based on the obtained pressure data.

The identification of the respective pressure state may then be used for initializing obtaining of blood flow data. Alternatively, the identification of the respective pressure state may then be used for selection of blood flow data for analysis. In accordance with this example, blood flow data corresponding to pre-set pressure intervals may be selected for analysis.

The method further comprises a step of assessing S9 the risk of pressure ulcers on the patient based on blood flow data obtained for at least two different expansion states of the expandable element. The blood flow for the different expansion states is analysed. When the blood flow during the pressure with the body weight against the support in the assessed skin area is greater than the blood flow during no pressure, there is less risk of pressure ulcers. When, on the other hand, the blood flow during the pressure with the body weight against the support in the assessed skin area is lower than the blood flow during no pressure, there is an increased risk of pressure ulcers.

There is generally less risk for pressure ulcers when a blood flow increases with the increased body pressure applied by the patient's weight. On the other hand, there is an increased risk for pressure ulcers when a blood flow decreases with increased body pressure applied by the patient's weight. Thus, the assessment of the risk of pressure ulcers on the patient involves determining whether the blood flow increases or decreases with increased body pressure applied to the assessed skin area by the patient's weight. Preferably, the increase or decrease of the blood flow is related to a basal blood flow, i.e. a blood flow measured unloaded.

As discussed above the assessment may for example be made based on obtained blood flow data obtained at discrete, predetermined pressure states, such as the first pressure state where no pressure is provided in the assessed skin area and the second pressure state where the body weight pressures against the assessed area, or based on continuously obtained blood flow data. In the first case, the obtained pressure data may be used for identifying S7 the discrete, predetermined pressure states. This identification may in turn be used for initiating blood flow measurements. The obtained pressure data may in the latter case be continuously associated to corresponding continuously obtained blood flow data. The obtained pressure data may then be used for selecting intervals of the blood flow data for the assessment of the risk of pressure ulcers.

Figure 2:
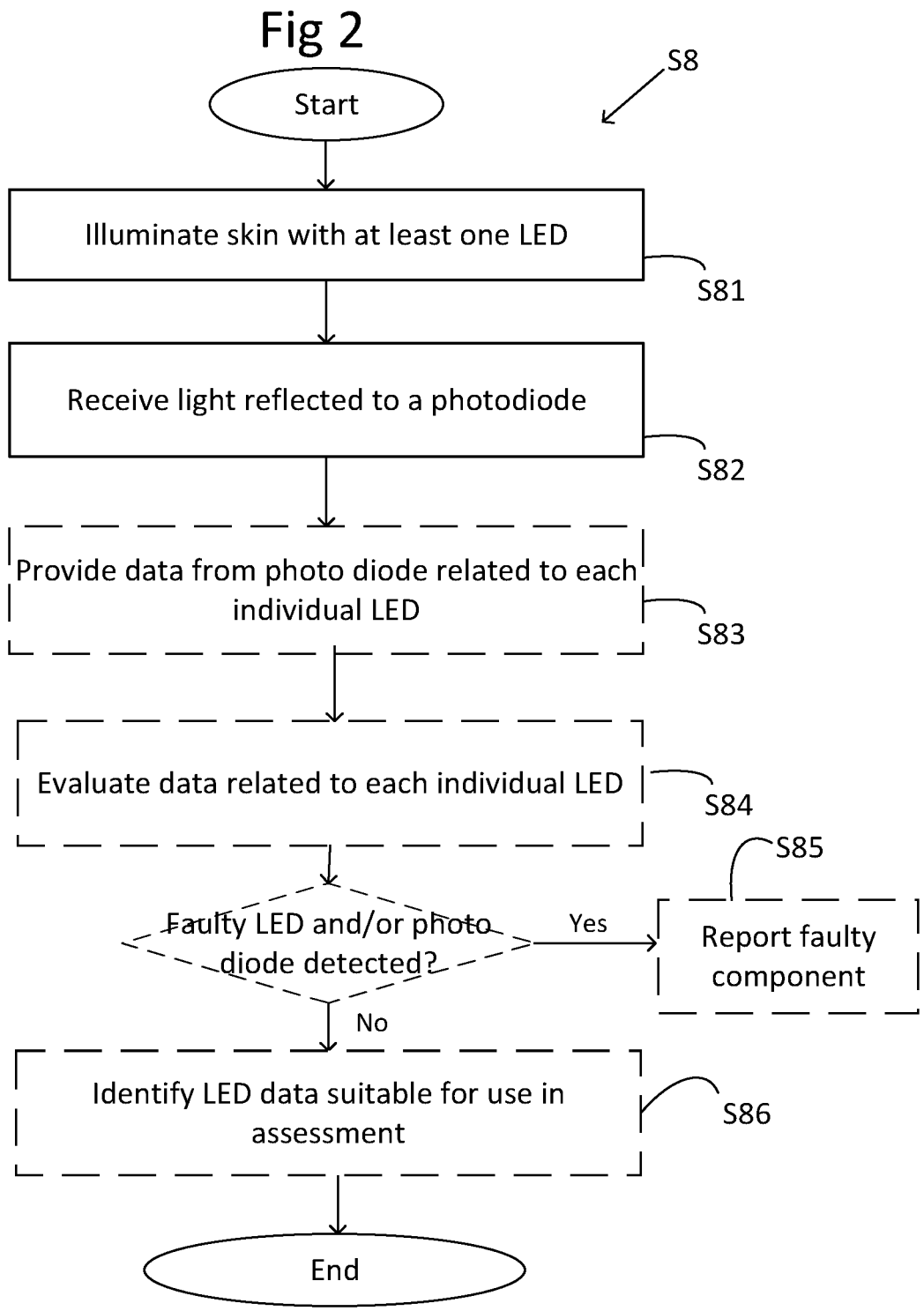
FIG. 2 is flow chart illustrating a step of obtaining blood flow data in a method for assessment of a blood flow for example according to FIG. 1.

FIG. 2 discloses examples of details of the step of obtaining S8 blood flow data related to an assessed skin area. The blood flow data is as discussed in relation to FIG. 1 obtained by means of photoplethysmography. The obtaining of blood flow data may comprise illuminating S81 the skin with the light from a LED, and measuring S82 the amount of light reflected to a photodiode. The LED and the photodiode form a blood flow sensor element. The blood flow sensor element may be arranged at a sensor plate. The LEDs may emit light having one wavelength. Alternatively, the LEDs may emit light having at least two different wavelengths. In accordance with the latter example, a first set of LEDs emitting at a first wavelength and a second set of LEDs emitting at a second wavelength may be illuminating the skin. The one or a plurality of photodiodes measuring the amount of light reflected thereto may each measure light originating from a plurality of LEDs. The data from each photodiode may be obtained such that that the contribution from each individual LED is identified S83 in the data from the respective photodiode.

The method may further comprise a step of evaluating S84 the data associated to each individual LED. Based on this evaluation it may be identified if any LED or photodiode is faulty. The evaluation may be performed by comparing the blood flow data to expected blood flow data for example defined by an upper and/or lower limit.

A detected faulty LED and/or photodiode may be reported S85.

The evaluation may also be performed so as to identify whether LEDs and/or photodiodes are not positioned correctly, for example not abutting against the skin.

A detected not correctly positioned LED and/or photodiode may be reported S85.

The method may further comprise a step of identifying S86 LED data suitable for use in assessment of the risk of pressure ulcers. The identification may comprise identifying LEDs giving rise to blood flow data deviating from the blood flow data obtained from other LEDs. The LEDs giving rise to deviating data may for example lack contact with the illuminated skin parts. The LEDs giving rise to the deviating data may then be removed from use in assessment of the risk of pressure ulcers.

Figure 3:
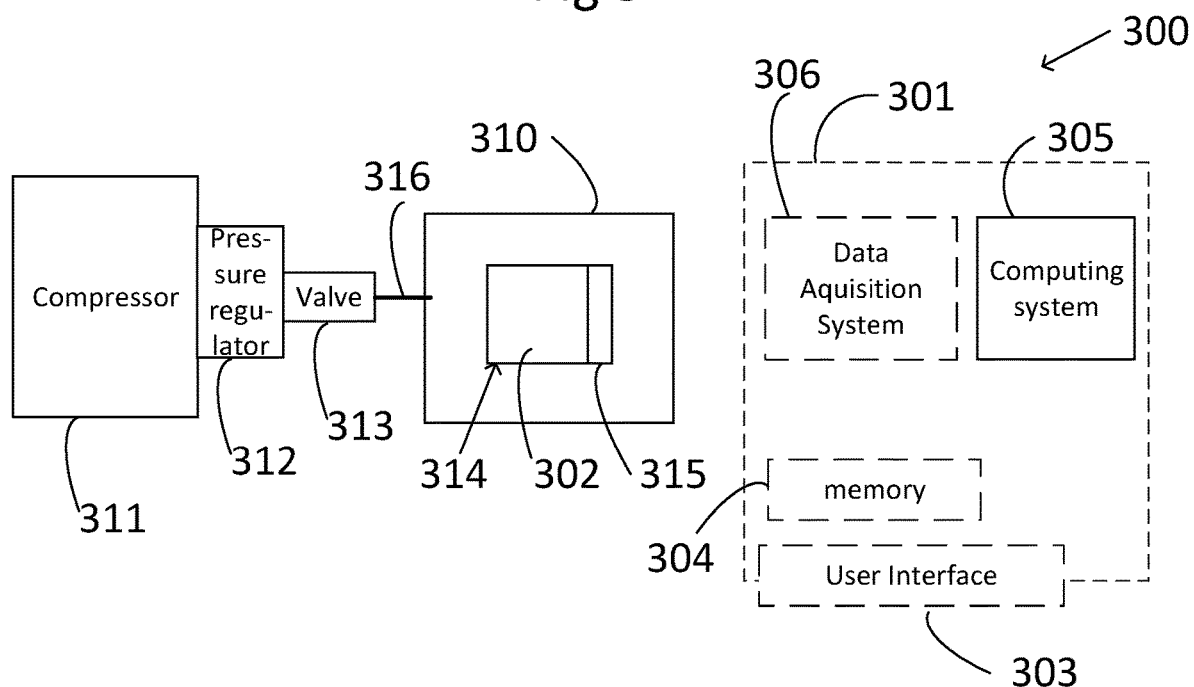
FIG. 3 is schematic sketch illustrating an example of a system for assessment of a tissue under pressure.

FIG. 3 discloses an example of a system 300 for an assessment of a blood flow an area of the skin and underlying tissue. The system 300 comprises a measurement system 314 including a sensor plate 302. The sensor plate is provided with at least one blood flow sensor element arranged to obtain blood flow data. The blood flow sensor elements may be formed by LEDs emitting light and photodiodes receiving the emitted light and returned from a reflection in the skin and underlying tissue. This has also been discussed in relation to FIGS. 2 and 1.

Further the system 300 may further comprise at least one pressure sensor 315. The pressure sensor 315 is in the illustrated example mounted at the sensor plate 302. The pressure sensor may then be arranged to sense a pressure exerted on the sensor plate. Alternatively, the pressure sensor 315 is separate component physically separated from the sensor plate and/or the blood flow sensor element.

An expansion element 310 having a controllable expansion state forms a frame at least partly bounding the sensor plate 302.

The expansion element may be designed in many different ways. The expansion element may for example be expandable by means of a gas, such as air, or liquid. The expandable element may be expandable by means of a mechanical solution. The expansion element may be expandable by means of a magnetic solution. The expandable element may be expandable by means of a chemical solution. The expandable element may comprise an intelligent textile having the expandable property.

The expandable element may be expanded and retracted over and over again. Alternatively, the expandable element is disposable. The disposable expandable element is characteristically only expandable/retractable once. For example, the expandable element may comprise an ampoule comprising a chemical compound when released being arranged to expand the expandable element.

In the illustrated example, the expandable element is an inflatable element. The inflatable element comprises an inflatable chamber, wherein an amount of air or another gas or the like is controllable. Accordingly, in the illustrated example, the system comprises a compressor 311 in communication with the inflatable element via a pressure regulator 312 and a valve 313.

In different examples, the inflatable element comprises an inflatable chamber, wherein the amount of air in the inflatable chamber is controlled to provide the controllable inflation. The inflatable element may be controlled to at least a first inflation state and a second inflation state by controlling the amount of air in the inflatable chamber.

The at least one pressure sensor may instead or in addition to measuring the body pressure applied by the patient's bodyweight in the assessed skin area be arranged to sense a pressure in the interior of the inflation element and/or a pressure applied over a pressure line 316 (not disclosed). These pressures may be used to determine the body pressure applied by the patient's bodyweight in the assessed skin area.

A computing system 305 is arranged to perform data processing of the blood flow data. The computing system 305 is arranged to assess the risk of pressure ulcers on a patient, based on the processed said blood flow data from at least two different inflation states of the inflatable chamber. Examples of this have been discussed in relation to FIGS. 1 and 2. In detail, the strength of the pulse of the body is measured by means of the blood flow data in at least two different inflation states. In one example the inflation states comprise a first state where substantially no pressure is applied and a second state where entire body weight pressures on the support in the assessed skin area. The measured pressure may be used for identification that the respective state has been reached.

The computing system may be arranged to control the inflation state. Alternatively, the inflation state is manually controlled. In the illustrated example, the inflation state is controlled by control of the pressure regulator, wherein the pressure regulator is manually controllable and/or controllable by the computing system 305.

The system 300 comprises in the illustrated example further a Data Acquisition System, DAS, 306 connected to the sensor plate 314 and to the computing system 305. The Data Acquisition System is arranged for data conditioning and converting of said blood flow data.

The system 300 may comprise a memory 304 for storage of the measured data used by the computing system 305. The memory 304 may further be arranged to store assessments made.

The system 300 comprises further a user interface 303. The user interface may be arranged to display information related to the assessment of the risk for pressure ulcers. For example, the result of the assessment may be presented by means of the user interface. The result may be a YES or NO, i.e. is there a risk of developing pressure ulcers. Alternatively, the risk may be presented as a percentage.

The user interface may further be arranged to present information related to the performance of the assessment. For example, if an individual LED or photodiode has been determined to be defected, this may be presented by means of the user interface. If the evaluation of the data obtained by the photo detectors reveals that the results obtained from measurements at different parts of the sensor plate differs, a warning may be presented. For example, this may indicate that at least some part of the sensor plate is not in abutment to the skin. The warning may then indicate that the measurement should be made again.

Figure 4:
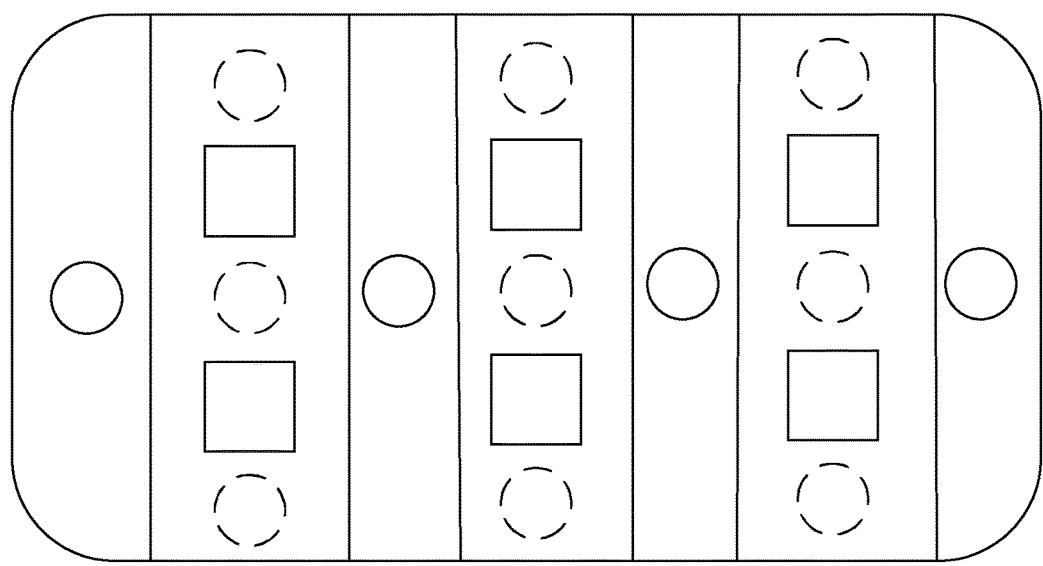
FIG. 4 illustrates schematically an example of a design of a sensor plate.

In FIG. 4, an example of a sensor plate is illustrated. The sensor plate may be flexible and arranged to follow the curvature of the skin. The sensor plate may be made of a material mild to the skin. The sensor plate may for example be made of rubber or a rubber based material.

In the illustrated example, the sensor plate is foldable along a plurality of collinear lines in order to be able to follow the curvature of the body. However, many other designs of the sensor plate may be considered enabling the sensor plate to follow the curvature of the body. Measurements may be improved if it can be secured that the sensor plate rest against the skin while making the measurements.

The sensor plate may at its side intended to face the skin be provided with an adhesive for attachment to the skin of the patient.

The sensor plate comprises a blood flow sensor element comprising a plurality of LEDs arranged to emit light at at least two different wavelengths. In one example, the LEDs may be arranged to emit red and green light. The blood sensor element further comprises at least one photodetector such as a photodiode. In the illustrated example, the blood flow sensor element further comprises a plurality of photodiodes arranged to receive the light emitted from the LEDs and reflected from the skin and underlying tissue. In the illustrated example, the blood flow sensor element comprises a plurality of LEDs emitting light which may be of at least two different wavelengths. Further, in the illustrated example, the blood flow sensor element comprises six photodiodes.

Each at least one photodetector may be arranged to receive data from a plurality of LEDs and to measure the data from each LED individually.

The sensor plate may further comprise at least one pressure sensor (not illustrated) arranged to measure the pressure caused by the body weight of a patient in the assessed skin area.

FIGS. 5a to 5c illustrate an example of an expansion element in accordance with this disclosure having a controllable expansion state. The expansion element has at least two different expansion states.

As discussed in relation to FIG. 3, the expansion element may be designed in many different ways. The expansion element may for example be expandable by means of a gas, such as air, or liquid. The expandable element may be expandable by means of a mechanical solution. The expansion element may be expandable by means of a magnetic solution. The expandable element may be chemically expandable. The expandable element may comprise an intelligent textile having the expandable property.

The expandable element may be expanded and retracted over and over again. Alternatively, the expandable element is disposable. The disposable expandable element is characteristically only expandable/retractable once. For example, a disposable expandable element may comprise an ampoule comprising a chemical compound when released being arranged to expand the expandable element.

The expandable element forms a frame designed to at least partly enclose the sensor plate.

The expansion element may be formed integrally with the sensor plate or being physically separated therefrom.

The expansion element may be formed integrally with the support on which the patient is intended to rest or it may be physically separated from the support. The support may be a bed.

In the view seen from above in FIG. 5a, it is disclosed that the expandable element forms a frame designed to at least partly enclose the sensor plate. Thus, the inflatable element comprises a rim enclosing an area.

In the side view of FIG. 5b it is disclosed that the expandable element when expanded is designed to extend above a sensor plate (dashed in the figure) when arranged in the area at least partly enclosed by the expandable element. Thereby, the rim protects the hollow area in the middle from pressure from a human body pressurizing against the expandable element.

In the side view of FIG. 5c it is disclosed that the expandable element when not expanded is designed to be as thin as possible. It may be desired that the expandable element in this state is essentially aligned with the support on which the expandable element is placed. Further, the upper surface of the expandable element may in this state be in the same plane as the surface of the sensor plate (dashed in the figure) when arranged in the area at least partly enclosed by the expandable element. Thereby, the expandable element does substantially not protect the area at least partly enclosed by the expandable element from the weight of a human body.

The invention claimed is:

1. A method for assessment of a blood flow in an assessed area of the skin and underlying tissue of a patient, said method comprising the steps of:
subjecting the assessed area of the skin and underlying tissue of the patient to at least two different pressures, wherein the different pressures are obtained by the weight of the patient pressuring against a support on which the patient is placed and an expandable element that circumvents the assessed area of the skin and underlying tissue of the patient, the expandable element forming a frame that entirely circumvents a sensor plate attached to the assessed area, and the entire frame being expandable in a direction from the support against the patient to substantially eliminate pressure on a body of the patient from the support in the assessed area, wherein subjecting the assessed area of the skin and underlying tissue of the patient to the at least two different pressures comprises controlling the entire frame circumventing the sensor plate at least between a first expansion state corresponding to a first pressure of the at least two pressures and a second expansion state corresponding to a second pressure of the at least two different pressures, wherein in the first expansion state the sensor plate entirely circumvented by the frame does not exert pressure on the support, and wherein in the second expansion state the sensor plate entirely circumvented by the frame exerts pressure on the support,
obtaining blood flow data related to the assessed area while subjecting the assessed area to the at least two different pressures, wherein the blood flow data is obtained by means of photoplethysmography, and assessing the risk of pressure ulcers on the patient based on an assessment of the blood flow data obtained for the at least two different pressures.

2. The method according to claim 1, wherein the first pressure of the at least two pressures is substantially zero.

3. The method according to claim 1, wherein the second pressure of the at least two different pressures is caused by the body weight pressures against the assessed area.

4. The method according to claim 1, further comprising a step of obtaining pressure data and identifying the respective pressures based on the obtained pressure data, wherein the step of assessing the risk of pressure ulcers is made based on the blood flow data obtained for the identified at least two different pressures.

5. The method according to claim 1, where the blood flow data is obtained by:
   illuminating the skin and underlying tissue with light from a LED,
   measuring the amount of the light reflected to a photodiode.

6. The method according to claim 1, said method comprising the steps of:
   providing the expandable element having a controllable expansion state,
   providing the sensor plate for obtaining the blood flow data using photoplethysmography, and
   positioning the expandable element in relation to the patient such that the weight of the patient provides the different pressures to the assessed area based on the expansion state of the expandable element.

7. The method according to claim 6, further comprising attaching the sensor plate to the skin of the assessed area.

8. The method according to claim 1, wherein the expandable element is integrally formed with the sensor plate.

9. The method according to claim 1, wherein the expandable element comprises a single, unitary expandable structure movable between only the first expansion state corresponding to the first pressure and the second expansion state corresponding to the second pressure.

10. The method of claim 1, wherein the first expansion state corresponds to the body of the patient spaced apart from the sensor plate, and wherein the second expansion state corresponds to the body of the patient in contact with the sensor plate.

11. A system for assessment of a blood flow in an assessed area of the skin and underlying tissue of a patient, said system comprising:
   a sensor plate having at least one blood flow sensor obtained by means of photoplethysmography;
   an expandable element, said expandable element being arranged to form a frame entirely circumventing the sensor plate;
   wherein the frame entirely circumventing the sensor plate ensures that the assessed area is subjected to at least two different pressures obtained by the weight of the patient pressuring against a support on which the patient is placed and an expansion of the entire frame entirely circumventing the sensor plate in a direction from the support against the patient to substantially eliminate a pressure on the body of the patient from the support in the assessed area; and
   a computing system arranged to perform data processing of blood flow data,
   wherein the at least one blood flow sensor is arranged to obtain the blood flow data while subjecting the assessed area to the at least two different pressures,
   wherein the computing system is arranged to assess the risk of pressure ulcers on the patient, based on assessment of the blood flow data for the at least two different pressures, and
   wherein the entire frame entirely circumventing the sensor plate is movable between a first expansion state corresponding to a first pressure of the at least two pressures and a second expansion state corresponding to a second pressure of the at least two pressures, wherein in the first expansion state the sensor plate entirely circumvented by the frame does not exert pressure on the support, and wherein in the second expansion state the sensor plate entirely circumvented by the frame exerts pressure on the support.

12. The system according to claim 11, further comprising a Data Acquisition System connected to the sensor plate, said Data Acquisition System being arranged for data conditioning and converting of said blood flow data, wherein the computing system is connected to the Data Acquisition System.

13. The system according to claim 11, wherein the sensor plate is flexible and arranged to follow the curvature of the skin.

14. The system according to claim 11, wherein the sensor plate is provided with an adhesive configured for attachment to the patient.

15. The system according to claim 11, where the sensor plate further comprises a plurality of light-emitting diodes (LEDs) of at least two different wavelengths and at least one photodetector.

16. The system according to claim 15, wherein the at least one photodetector is arranged to receive data from the plurality of LEDs and to measure the data from each LED individually.

17. The system according to claim 11, further comprising at least one pressure sensor obtaining pressure data, wherein the computing system is arranged to identify the respective pressures based on the obtained pressure data and to assess the risk of pressure ulcers on the patient based on the blood flow data obtained for the at least two different pressures.

18. The methed system according to claim 11, wherein the expandable element is integrally formed with the sensor plate.

19. A method for assessment of a blood flow in an assessed area of the skin and underlying tissue of a patient, said method comprising the steps of:
   subjecting the assessed area of the skin and underlying tissue of the patient to at least two different pressures, wherein the different pressures are obtained by the weight of the patient pressuring against a support on which the patient is placed and a single expandable element that at least partly circumvents the assessed area of the skin and underlying tissue of the patient, the single expandable element forming a frame that entirely circumvents a sensor plate attached to the assessed area,
   the entire frame being expandable in a direction from the support against the patient to substantially eliminate pressure on a body of the patient from the support in the assessed area,
   obtaining blood flow data related to the assessed area while subjecting the assessed area to the at least two different pressures, wherein a first pressure of the at least two pressures is substantially zero and a second pressure of the at least two pressures corresponds with a weight of the body of the patient on the assessed area, and wherein the blood flow data is obtained by means of photoplethysmography, and assessing the risk of pressure ulcers on the patient based on an assessment of the blood flow data obtained for the at least two different pressures, and wherein the single expandable element is controllable between a first expansion state corresponding to the first pressure and a second expansion state corresponding to the second pressure, wherein in the first expansion state the sensor plate entirely circumvented by the frame does not exert pressure on the support, and wherein in the second expansion state the sensor plate entirely circumvented by the frame exerts pressure on the support.

20. The method of claim 19, wherein the first expansion state corresponds to the body of the patient spaced apart from the sensor plate, and wherein the second expansion state corresponds to the body of the patient in contact with the sensor plate.

* * * * *